United States Patent [19]

Mammone et al.

[11] Patent Number: 5,800,826
[45] Date of Patent: Sep. 1, 1998

[54] SUNSCREEN COMPOSITIONS CONTAINING DAMAGED RNA FRAGMENTS

[75] Inventors: Thomas Mammone, Farmingdale; Michael Ingrassia, Brentwood, both of N.Y.

[73] Assignee: E-L Management Corp., New York, N.Y.

[21] Appl. No.: 811,892

[22] Filed: Mar. 5, 1997

[51] Int. Cl.⁶ .................................................. A61K 7/00
[52] U.S. Cl. ........................ 424/401; 424/59; 424/70.9; 514/44; 532/23.1
[58] Field of Search ................ 424/401, 59, 70.9; 514/44; 532/23.1

[56] References Cited

U.S. PATENT DOCUMENTS 5,470,577  11/1995  Gilchrest et al. ................ 424/450
5,532,001  7/1996  Gilchrest et al. ................ 424/450

FOREIGN PATENT DOCUMENTS 2233557  1/1991  United Kingdom .
95/01773  1/1995  WIPO .
96/01617  1/1996  WIPO .

OTHER PUBLICATIONS

Choay, *Chemical Abstracts*, vol. 72, #58993.

*Primary Examiner*—Thurman K. Page
*Assistant Examiner*—Pamela S. Webber
*Attorney, Agent, or Firm*—Karen A. Lowney, Esq.

[57] ABSTRACT

The present invention relates to a protection-effective amount of UV-damaged RNA fragments, in combination with a cosmetically or pharmaceutically acceptable carrier. The compositions are useful in the prevention of skin damage to UV radiation and in preventing photoaging.

22 Claims, No Drawings

SUNSCREEN COMPOSITIONS CONTAINING DAMAGED RNA FRAGMENTS

FIELD OF THE INVENTION

The present invention relates to the field of sunscreens. More specifically, the invention relates to sunscreen and cosmetic compositions containing RNA, which provides protection against damaging solar radiation.

BACKGROUND OF THE INVENTION

It has now been well established that long-term exposure to the sun increases the risk of a number of undesirable skin conditions. Not only has solar radiation been implicated as a causative agent of a number of skin cancers, it has also been shown to accelerate the aging process, causing a variety of effects, such as lines, wrinkles, spots, and loss of skin tone. Ironically, the public's increasing awareness of the importance of exercise and athletic activity to a healthy life has probably led to an increase in outdoor activities, and consequently, more people being exposed to larger doses of sunlight than would otherwise be recommended, notwithstanding the widespread knowledge of the danger of sun exposure. It has therefore become a priority to develop sunscreens which provide an adequate level of protection against solar damage.

There are now available a number of sunscreens and cosmetic products which do provide significant protection against the effects of the sun's rays. Many of the most commonly used sunscreens, for example para-amino benzoic acid(PABA) and its esters, benzophenones, and cinnamates are chemical sunscreens, i.e., synthetic chemicals that are not found in nature. Although many of these materials are quite protective, and can be used by a large proportion of the target population, there is a significant segment of the population which will not, or for reasons of sensitivity or allergic reaction, cannot, use chemical sunscreens. These individuals demand a sunscreen which is natural, i.e., routinely found in nature. There has, therefore, been a recent trend to seeking out natural sunscreens.

Among the naturally occurring materials which have received attention are nucleic acids, in particular DNA and RNA. For example, U.S. Pat. Nos. 5,470,577 and 5,532,001 discloses the use of DNA fragments, in particular single-stranded) DNA fragments, double-stranded DNA fragments, mixtures thereof, deoxynucleotides, dinucleotides and dinucleotide dimers for the stimulation of melanin synthesis in epidermal cells, which, according to the cited patent, provides protection against UV radiation. In addition, WO 9601617 states that nucleic acids can provide a barrier to UV radiation, and suggests that they may be used in topical compositions. GB 2233557 also discloses a cytoprotecting agent which contains RNA, ribonucleotides or ribonucleosides, and salts or other derivatives thereof, the agent said to provide protection to skin against the affects of light.

It has not previously been reported to use irradiated fragments of RNA to provide protection to UV-exposed cells. It has now been discovered that UV-damaged RNA fragments added to skin cells unexpectedly can induce repair or UV resistance to these cells when exposed to a subsequent UV insult. As such, the damaged RNA fragments are a useful component of sunscreen compositions and other skin products in which provision of a measure of UV protection is desirable.

SUMMARY OF THE INVENTION

The present invention relates to cosmetic or pharmaceutical compositions comprising a protection-effective amount of UV-damaged RNA fragments, in combination with a cosmetically or pharmaceutically acceptable carrier. The invention further relates to a method for protecting skin cells from UV damage which comprises applying to the skin cells a protection-effective amount of UV-damaged RNA fragments. In addition, the invention relates to a method for prevention of photoaging of skin, which comprises applying to the skin an effective amount of UV-damaged RNA fragments.

DETAILED DESCRIPTION OF THE INVENTION

The invention is predicated on the discovery that UV-damaged RNA fragments, when applied to living skin cells, increase the survival rate of the treated cells, compared with untreated cells, when the cells are subsequently exposed to UV radiation. In particular, it has been noted that the damaged RNA generated from treatment of whole RNA with UV radiation offers treated cells considerable protection from the cytotoxic effects of UVB radiation. The level of protection provided is greater than that provided by unirradiated RNA.

The RNA used in the invention can be from any source and can be of any type. For example, it may be obtained from plant, animal, or microbial sources, and may be messenger RNA(mRNA), transfer RNA(tRNA), mitochondrial RNA(mtRNA), viral RNA, or synthetic RNA. In a preferred embodiment, whole RNA is irradiated with UVC (wavelength of about 254 nm) for a period of at least about 3 minutes, and preferably for at least 5 minutes. Other UV wavelengths can also be used in irradiating the RNA, but the dosage of will be higher. In a particularly preferred embodiment, the RNA employed is substantially pure, i.e., at least about 90% free of non-RNA material. The UV treatment results in a fragmentation of the RNA.

Fragments prepared as described above were applied to plated epidermal skin cells at an amount of about 1 μ/ml, with unirradiated RNA used as a control, and then the plates exposed to UVB radiation at a level of from 0 to 75 mJ at 15 mJ intervals. After an overnight incubation, the cells treated with the irradiated RNA were found to have protected the skin cells from the damaging effects of UV radiation. Although unirradiated RNA also provide some apparent measure of protection, the protection provided by the irradiated RNA is significantly higher.

The fragments of the present invention can be incorporated into a variety of cosmetic or pharmaceutical products. For example, fragments can be added as a sunscreen component to makeup compositions, such as lipsticks, eyeshadows, foundations, or any other type of composition intended to be worn on the skin outdoors, e.g., a moisturizer or lip balm, where UV protection is desirable. The fragments are also useful as an active component of sunscreen compositions. The fragments are water soluble, and can be routinely incorporated into the formulation of interest in any manner known in the art. In a preferred embodiment, the fragments, when used in purified form, are added in an amount of from about 0.001–5%, preferably about 0.5–3%, by weight of the total composition.

The fragments of the invention can also be used in combination with other sun protection materials. Thus, in another embodiment, the fragments are combined with one or more other sunscreens of any type. The second sunscreen may be of the physical barrier type, e.g., titanium dioxide or zinc oxide, or the chemical type, e.g., benzophenones; para-amino benzoic acid(PABA) and its derivative; phenyl or homomenthyl salicylate; or cinnamates. The combination is useful in any situation in which the fragments alone could be used, e.g., in a makeup formulation, a sunscreen formulation or self-tanning formulation. The additional sunscreen can be incorporated into the formulation in amount determined in accordance with its usual usage.

In a further embodiment, the fragments are also combined with antioxidants or free-radical scavengers, which provide supplementary protection against UV-induced skin damage. Examples of such materials include Vitamin E and derivatives thereof, Vitamin C and derivatives thereof, green tea extract, proanthocyanidins, β-carotene and the like.

In an additional embodiment, the RNA fragments are also useful in prevention of photoaging. As noted above, repeated and/or prolonged exposure to the sun's UV radiation contributes substantially to premature decline in the quality and quantity of elastin and collagen in the skin. These changes are manifested externally by typical signs of aging, such as deep lines and wrinkles, loss of elasticity, skin dryness and unevenness, and increased frequency of blotches or pigmented spots. The UV-protection provided by the fragments of the invention can also provide the desired protection against photoaging. Thus, in addition to the use as a sunscreen in the products noted above, the fragments alone can be used to prevent photoaging when used in a variety of skin products, such as those described above.

In this regard, the irradiated fragments can also be combined with other anti-aging or skin-enhancing agents. For this purpose, the fragments can be combined with one or more of the following products: alpha- or beta-hydroxy acids, such as lactic acid, glycolic acid, citric acid, alpha-hydroxyoctanoic acid, alpha-hydroxydecanoic acid, alpha-hydroxylauric acid, tartaric acid, glucouronic acid, galacturonic acid, alpha-hydroxybutyric acid, alpha-hydroxyisobutyric acid, malic acid, mandelic acid, pyruvic acid, and tartronic acid, and salicylic acid; retinoids, such as retinol, retinyl acetate, retinyl palmitate, retinyl butyrate, retinyl oleate, retinyl linoleate, and retinoic acid; DHEA and derivatives thereof.

The invention is further illustrated by the following non-limiting examples.

EXAMPLES

I. Enhancement of Irradiated Cell Viability

A. MATERIALS AND METHODS

1. Preparation of RNA fragments

Twenty micrograms of messenger RNA(mRNA) purchased from Sigma is solubilized in one ml of PBS. The solubilized RNA is split into two 0.5 ml aliquots, each of which is placed into a 35 mm petri dish. One aliquot is irradiated with UVC at 254 nm for a period of five minutes, while the other sample remains unexposed to UV radiation. Each sample is then further diluted by adjusting the volume to 10 ml in 10% DMEM, to yield a final concentration of 1 µ/ml. The stock solutions are then added either neat, or are further diluted to yield final concentrations of 0.1, 0.5 or 1 µg/ml per ml.

2. Treatment of skin cells

Hacat skin cells(transformed human keratinocytes) are seeded into two 96 well plates, and allowed to reach approximately 75% confluence prior to treatment. The prepared RNA solutions are added to individual wells, and incubated overnight, humidified, at 37° C., and 5% carbon dioxide. Plates are then rinsed three times with 180 µl PBS, and are irrigated with 100 µl PBS during irradiation. Plates are irradiated with UVB, from 0 to 75 mJ/cm² at 15 mJ intervals. Following irradiation, PBS is aspirated, and the mRNA solution is added as described above. After an overnight incubation at 37° C., plates are assayed for cell viability using the neutral red dye uptake assay.

B. RESULTS

Tables 1a and 2a show the results obtained using unirradiated(1) and irradiated(2) mRNA as protectant, the results being expressed as percentage survival after irradiation. Tables 1b and 2b shows the percentage change in survival rate for each treatment relative to the unirradiated control.

TABLE 1a

| | AVERAGE ABSORBANCE | | | | | |
|---|---|---|---|---|---|---|
| mJ UVB | 0 | 15 | 30 | 45 | 60 | 75 |
| control | 0.495 | 0.485 | 0.448 | 0.391 | 0.315 | 0.262 |
| .1 µg/ml | 0.573 | 0.524 | 0.483 | 0.412 | 0.352 | 0.287 |
| .5 µg/ml | 0.575 | 0.509 | 0.490 | 0.435 | 0.380 | 0.293 |
| 1 µg/ml | 0.598 | 0.549 | 0.509 | 0.441 | 0.359 | 0.292 |

TABLE 1b

| | % CHANGE | | | | | |
|---|---|---|---|---|---|---|
| mJ UVB | 0 | 15 | 30 | 45 | 60 | 75 |
| control | | | | | | |
| .1 µg/ml | 15.6 | 8.0 | 7.6 | 5.4 | 11.7 | 9.8 |
| .5 µg/ml | 16.1 | 4.9 | 9.3 | 11.3 | 20.4 | 12.1 |
| 1 µg/ml | 20.6 | 13.2 | 13.5 | 12.7 | 14.0 | 11.6 |

TABLE 2a

| | AVERAGE ABSORBANCE | | | | | |
|---|---|---|---|---|---|---|
| mJ UVB | 0 | 15 | 30 | 45 | 60 | 75 |
| control | 0.413 | 0.353 | 0.358 | 0.273 | 0.238 | 0.238 |
| .1 µg/ml | 0.473 | 0.408 | 0.344 | 0.304 | 0.301 | 0.268 |
| .5 µg/ml | 0.467 | 0.480 | 0.456 | 0.396 | 0.379 | 0.260 |
| 1 µg/ml | 0.468 | 0.444 | 0.511 | 0.398 | 0.355 | 0.301 |

TABLE 2b

| | % CHANGE | | | | | |
|---|---|---|---|---|---|---|
| mJ UVB | 0 | 15 | 30 | 45 | 60 | 75 |
| control | | | | | | |
| .1 µg/ml | 14.7 | 15.5 | −4.0 | 11.0 | 26.7 | 12.9 |
| .5 µg/ml | 13.2 | 35.9 | 27.4 | 44.9 | 59.5 | 9.4 |
| 1 µg/ml | 13.5 | 25.5 | 42.6 | 45.4 | 49.1 | 26.8 |

These results show a significant difference in survival rate of the cells treated with irradiated RNA fragments as compared with the cells treated only with unirradiated RNA, and therefore, demonstrate the protective effect of the irradiated RNA fragments.

II. Preparation of an RNA Fragment-Containing Formulation

The following is an example of a formulation containing RNA fragments of the invention:

| MATERIAL | WEIGHT % |
| --- | --- |
| Stearic acid | 2.4 |
| glyceryl monostearate | 2.2 |
| butyl paraben | 0.1 |
| Mineral oil/Lanolin alcohol (Amerchol) | 9.5 |
| Petrolatum/Lanolin alcohol | 2.0 |
| Sesame oil | 4.3 |
| Propyl paraben | 0.1 |
| deionized water | QS |
| triethanolamine 99% | 0.82 |
| methyl paraben | 0.3 |
| Trisodium EDTA | 0.1 |
| propylene glycol | 4.3 |
| purified mRNA | 0.001 |

What we claim is:

1. A cosmetic or pharmaceutical composition comprising a protection-effective amount of UV-damaged RNA fragments, in combination with a cosmetically or pharmaceutically acceptable carrier.

2. The composition of claim 1 in which the fragments are UVC-damaged.

3. The composition of claim 1 in which the RNA is messenger RNA.

4. The composition of claim 2 in which the fragments are present in an amount of from about 0.001 to 5% by weight.

5. The composition of claim 4 in which the fragments are present in an amount of from about 0.5%–3%.

6. The composition of claim 1 in which the composition is a sunscreen.

7. The composition of claim 1 which further comprises at least one additional sunscreen agent.

8. The composition of claim 1 in which the composition is a makeup selected from the group consisting of a lipstick, foundation, powder, or eyeshadow.

9. The composition of claim 1 in which the composition is a moisturizer or lip balm.

10. The composition of claim 1 which further comprises an antioxidant.

11. A method for protecting skin cells from UV damage which comprises applying to the skin cells a composition comprising a protection-effective amount of UV-damaged RNA fragments.

12. The method of claim 10 in which the fragments are UVC-damaged.

13. The method of claim 1 in which the RNA is messenger RNA.

14. The method of claim 12 in which the fragments are present in an amount of from about 0.001 to 5%.

15. The method of claim 14 in which the fragments are present in an amount of from about 0.5% to 3%.

16. The method of claim 11 in which the fragments are combined with a sunscreen agent.

17. The method of claim 11 in which the fragments are combined with an antioxidant.

18. A method of preventing photoaging which comprises applying to the skin a composition comprising a protection-effective amount of UV-damaged RNA fragments.

19. The method of claim 18 in which the fragments are UVC-damaged.

20. The method of claim 18 in which the RNA is messenger RNA.

21. The method of claim 19 in which the fragments are present in the composition in an amount of from about 0.001 to 5% by weight.

22. The method of claim 21 in which the fragments are present in an amount of from about 0.5% to 3%.

* * * * *